(12) United States Patent
Fridshtand et al.

(10) Patent No.: US 8,858,646 B2
(45) Date of Patent: Oct. 14, 2014

(54) HIP STEM PROSTHESIS

(75) Inventors: Natalia Fridshtand, Ringwood, NJ (US); Douglas W. Gabel, Pompton Plains, NJ (US); Steven J. Charlebois, West Lafayette, IN (US); David L. Glass, Silver Lake, IN (US); Steven A. Zawadzki, Leesburg, IN (US); Jeffrey P. Matney, Pierceton, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 13/465,172

(22) Filed: May 7, 2012

(65) Prior Publication Data

US 2012/0221116 A1 Aug. 30, 2012

Related U.S. Application Data

(63) Continuation of application No. 12/880,365, filed on Sep. 13, 2010, now Pat. No. 8,206,455, which is a continuation of application No. 11/063,030, filed on Feb. 22, 2005, now Pat. No. 7,842,096.

(51) Int. Cl.
*A61F 2/36* (2006.01)
*A61F 2/30* (2006.01)

(52) U.S. Cl.
CPC ... *A61F 2/30767* (2013.01); *A61F 2002/30332* (2013.01); *A61F 2002/30981* (2013.01); *A61F 2/3672* (2013.01); *A61F 2002/3625* (2013.01); *A61F 2230/0067* (2013.01); *A61F 2220/0033* (2013.01); *A61F 2002/30322* (2013.01); *A61F 2/3662* (2013.01); *A61F 2230/0017* (2013.01); *A61F 2230/0006* (2013.01); *A61F 2250/0026* (2013.01); *A61F 2310/00544* (2013.01); *A61F 2230/0026* (2013.01); *A61F 2002/365* (2013.01); *A61F 2/36* (2013.01); *A61F 2/3676* (2013.01); *A61F 2/367* (2013.01); *A61F 2002/30113* (2013.01); *A61F 2002/30795* (2013.01); *A61F 2002/30123* (2013.01); *A61F 2002/30205* (2013.01); *A61F 2002/30112* (2013.01); *A61F 2002/30143* (2013.01); *A61F 2002/30158* (2013.01); *A61F 2230/0004* (2013.01)
USPC .............. 623/23.24; 623/23.3; 623/23.35

(58) Field of Classification Search
CPC .................................................. A61F 2002/369
USPC ............. 623/20.35–20.36, 22.11, 22.4–23.38
See application file for complete search history.

(56) References Cited

U.S. PATENT DOCUMENTS

| | | | |
|---|---|---|---|
| 4,536,894 A | 8/1985 | Galante et al. | |
| 4,650,489 A | 3/1987 | Thompson | |

(Continued)

FOREIGN PATENT DOCUMENTS

| | | |
|---|---|---|
| FR | 2678509 A3 | 1/1993 |
| FR | 2683450 A1 | 5/1993 |

(Continued)

OTHER PUBLICATIONS

Machine Translation of FR 2853524 A1, pp. 1-6, Sep. 23, 2013.*

(Continued)

*Primary Examiner* — Thomas J Sweet
*Assistant Examiner* — Rebecca Preston
(74) *Attorney, Agent, or Firm* — Schwegman Lundberg & Woessner, P.A.

(57) ABSTRACT

A hip prosthesis is provided for insertion into a femur. In one exemplary embodiment, the hip prosthesis includes a stem having a proximal end, a distal end, and a longitudinal axis. This stem may include anterior and posterior locking surfaces which diverge away from the longitudinal axis. A shank portion may extend distally from the anterior and posterior locking surfaces and converge at an angle distally toward the longitudinal axis.

20 Claims, 3 Drawing Sheets

(56) References Cited

U.S. PATENT DOCUMENTS

| | | | |
|---|---|---|---|
| 4,792,339 | A | 12/1988 | Tepi |
| 4,813,963 | A | 3/1989 | Hori et al. |
| 4,895,573 | A | 1/1990 | Koenerman et al. |
| 5,007,931 | A | 4/1991 | Smith |
| 5,236,457 | A | 8/1993 | Devanathan |
| 5,316,550 | A | 5/1994 | Forte |
| 5,443,512 | A | 8/1995 | Parr et al. |
| 5,593,451 | A | 1/1997 | Averill et al. |
| 5,702,487 | A | 12/1997 | Averill |
| 5,863,295 | A | 1/1999 | Averill |
| 6,136,035 | A | 10/2000 | Lob et al. |
| 6,165,177 | A | 12/2000 | Wilson et al. |
| 6,190,417 | B1 | 2/2001 | Itoman et al. |
| 6,395,327 | B1 | 5/2002 | Shetty |
| 6,514,288 | B2 | 2/2003 | Meulink et al. |
| 6,576,014 | B2 | 6/2003 | Shetty |
| 6,676,706 | B1 | 1/2004 | Mears et al. |
| 6,685,987 | B2 | 2/2004 | Shetty |
| 6,695,884 | B1 | 2/2004 | Townley |
| 6,994,731 | B2 | 2/2006 | Howie |
| 7,001,672 | B2 | 2/2006 | Justin et al. |
| 7,497,875 | B1 | 3/2009 | Zweymüller |
| 7,842,096 | B2 | 11/2010 | Fridshtand et al. |
| 8,206,455 | B2 | 6/2012 | Fridshtand et al. |
| 2003/0074080 | A1 | 4/2003 | Murray |
| 2003/0232124 | A1 | 12/2003 | Medlin et al. |
| 2004/0010319 | A1 | 1/2004 | McTighe et al. |
| 2004/0107001 | A1 | 6/2004 | Cheal et al. |
| 2005/0048193 | A1 | 3/2005 | Li et al. |

FOREIGN PATENT DOCUMENTS

| | | | | |
|---|---|---|---|---|
| FR | 2683450 | B1 | 5/1997 | |
| FR | 2853524 | A1 * | 10/2004 | ............... A61F 2/36 |
| GB | 2216425 | A | 10/1989 | |
| WO | WO94/16649 | A1 | 8/1994 | |
| WO | WO94/20046 | A1 | 9/1994 | |
| WO | WO97/41809 | A1 | 11/1997 | |
| WO | WO00/59410 | A2 | 10/2000 | |

OTHER PUBLICATIONS

Zimmer, Inc., VerSys Hip System, Fiber Metal Taper Hip Prosthes, Versatile Total Hip Solutions Using Proven Designs and Enhanced Fixation, 97-7862-01 20MIP, 1997.

Zimmer, Inc., VerSys Hip System, LD/Fx Hip Prostheses, Versatile Solutions for Total and Partial Hip Replacement, 97-7831-01 Rev. 1, 15MM, 1998.

Brochure—Zimmer VerSys Hip System, Cemented Hip Prosthesis, Traditional Design, Innovative Features, 97-7853-01 16MIL, Zimmer, Inc. 1999.

Surgical Technique—Zimmer VerSys Cemented, Cemented Plus, and Cemented CT Hip Prostheses, Zimmer, Inc., 7 pages.

"Trapezoid" Merriam-Webster Dictionary Nov. 20, 2009, p. 1.

Surgical Technique—Zimmer Epoch® Hip Prosthesis 97-4075-02 Rev, Zimmer, Inc. 2002, 14 pages.

Brochure—Zimmer Epoch® Hip Prosthesis 97-4075-01 Rev, Zimmer, Inc. 2002, 8 pages.

Page, John "Included Angle" 2007. The Math Open Reference Project. http://www.mathopenref.com/angleincluded.html.

Webpage—Zimmer Epoch® Hip Prosthesis www.zimmer.com, 2007 Zimmer, Inc.—accessed Mar. 13, 2008.

Office Action mailed Jun. 13, 2007 in related U.S. Appl. No. 11/063,030.

Response to Office Action filed Nov. 13, 2007 in related U.S. Appl. No. 11/063,030.

Final Office Action mailed Feb. 7, 2008 in related U.S. Appl. No. 11/063,030.

Response to Office Action filed Jun. 6, 2008 in related U.S. Appl. No. 11/063,030.

Office Action mailed Sep. 30, 2008 in related U.S. Appl. No. 11/063,030.

Response to Office Action filed Dec. 30, 2008 in related U.S. Appl. No. 11/063,030.

Office Action mailed Apr. 8, 2009 in related U.S. Appl. No. 11/063,030.

Response to Office Action filed Jul. 8, 2009 in related U.S. Appl. No. 11/063,030.

Final Office Action mailed Nov. 24, 2009 in related U.S. Appl. No. 11/063,030.

Response to Office Action filed Feb. 24, 2010 in related U.S. Appl. No. 11/063,030.

312 Amendment filed Aug. 18, 2010 in related U.S. Appl. No. 11/063,030.

Office Action mailed Mar. 1, 2011 in related U.S. Appl. No. 12/880,365.

Response to Office Action filed May 19, 2011 in related U.S. Appl. No. 12/880,365.

Office Action mailed Aug. 3, 2011 in related U.S. Appl. No. 12/880,365.

Response to Office Action filed Nov. 8, 2011 in related U.S. Appl. No. 12/880,365.

Supplemental Response to Office Action filed Nov. 8, 2011 in related U.S. Appl. No. 12/880,365.

Final Office Action mailed Feb. 16, 2012 in related U.S. Appl. No. 12/880,365.

Response to Office Action filed Apr. 13, 2012 in related U.S. Appl. No. 12/880,365.

"U.S. Appl. No. 11/063,030, Advisory Action mailed Mar. 11, 2010", 3 pgs.

"U.S. Appl. No. 11/063,030, Notice of Allowance mailed Jul. 29, 2010", 7 pgs.

U.S. Appl. No. 11/063,030, Response to Rule 312 Communication mailed Sep. 13, 2010, 2 pgs.

"U.S. Appl. No. 12/880,365, Notice of Allowance mailed Apr. 27, 2012", 7 pgs.

"Zimmer VerSys Hip System Cemented Hip Prosthesis", Traditional Design, Innovative Features, 97-7853-01 16MIL, Zimmer, Inc, (1999), 4 pgs.

* cited by examiner

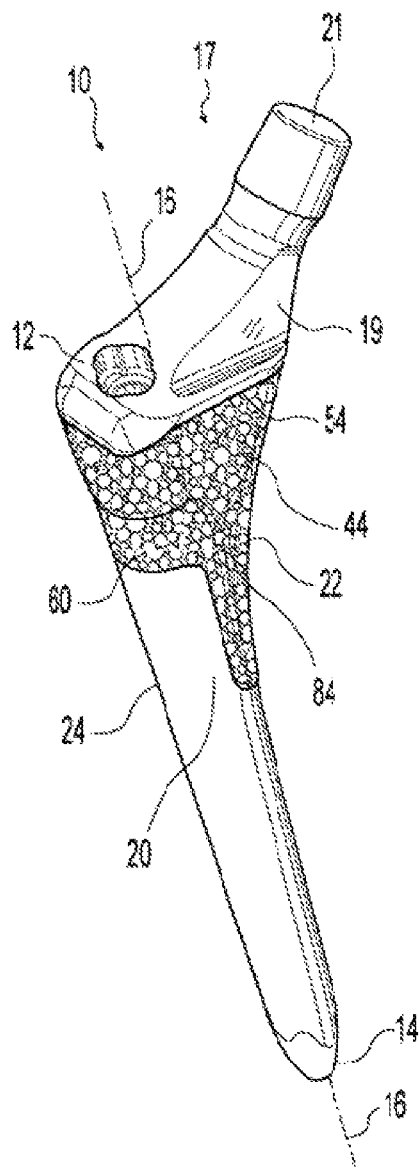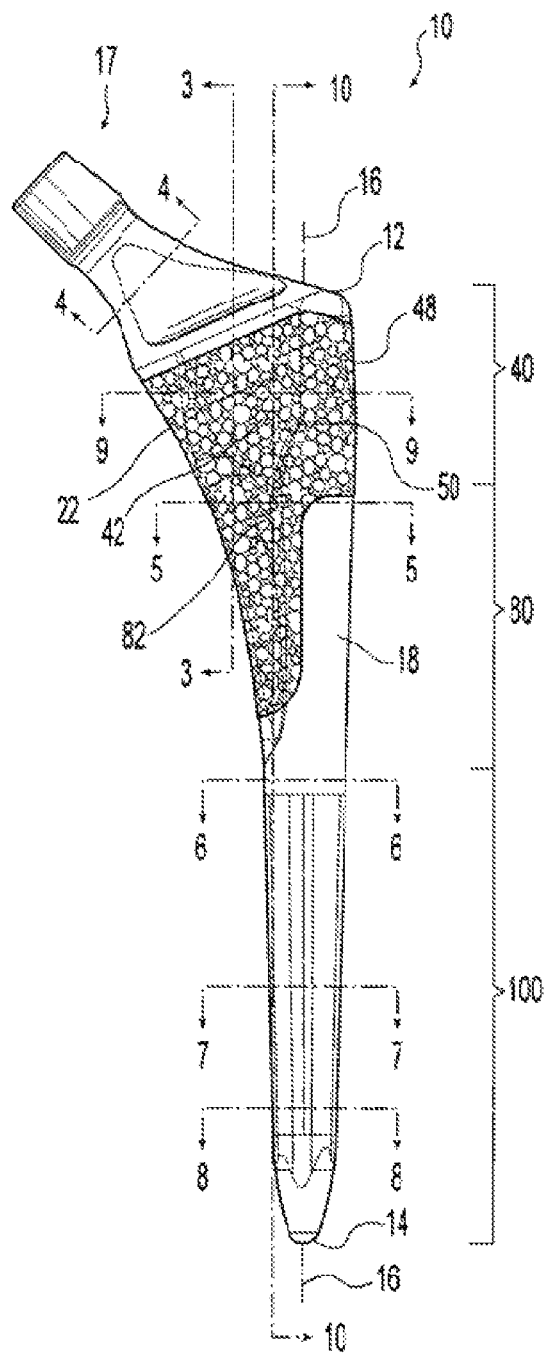
Fig. 1
Fig. 2

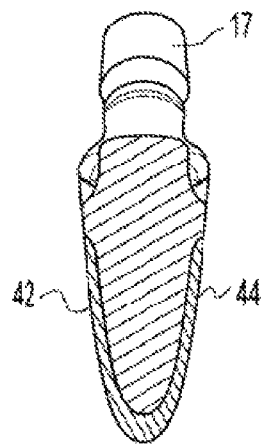
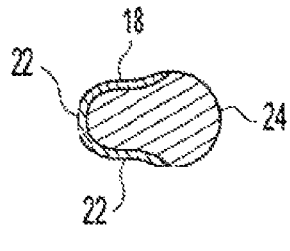
Fig. 3
Fig. 4
Fig. 5
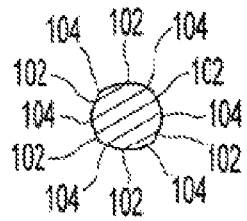
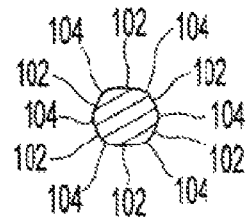
Fig. 6
Fig. 7
Fig. 8
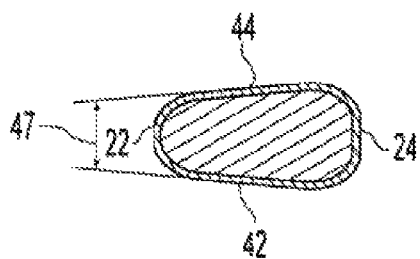
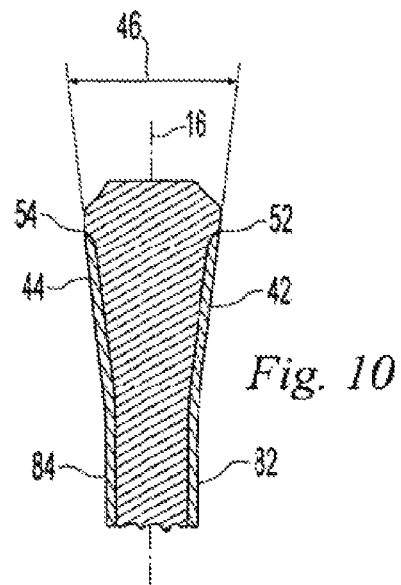
Fig. 9
Fig. 10

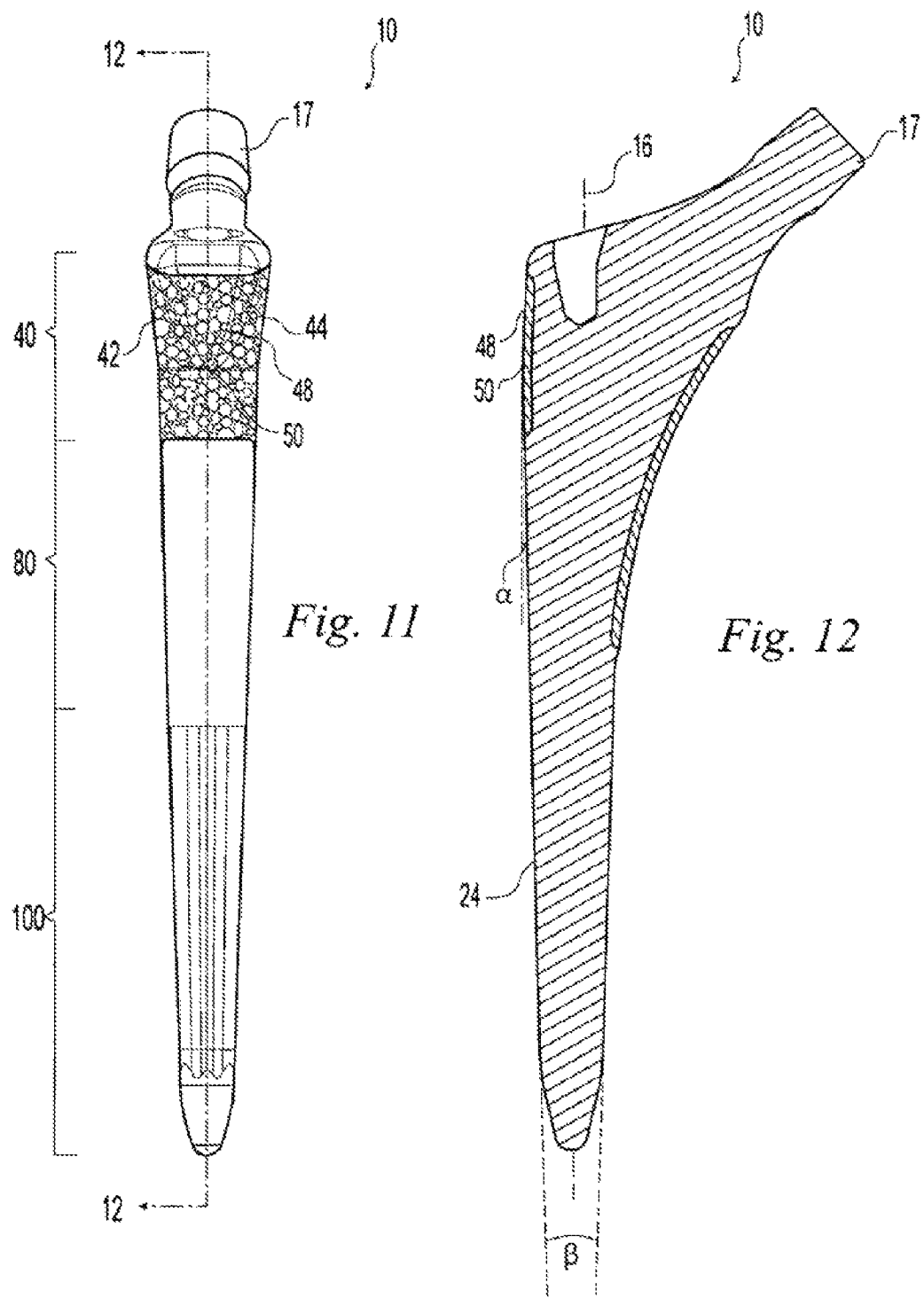

HIP STEM PROSTHESIS

CROSS REFERENCE TO RELATED APPLICATIONS

This application is a continuation of U.S. patent application Ser. No. 12/880,365, filed Sep. 13, 2010, now U.S. Pat. No. 8,206,455 which is a continuation of U.S. patent application Ser. No. 11/063,030, filed Feb. 22, 2005, now U.S. Pat. No. 7,842,096, the disclosures of which are hereby expressly incorporated by reference herein in their entirety.

FIELD OF THE INVENTION

The invention relates to orthopaedic implants. In particular, this invention relates to hip stem prostheses.

BACKGROUND

Total hip arthroplasty is often used to restore function to a diseased or injured hip joint. Positions and directions relative to the hip joint may be described in terms of proximal being nearer the hip joint, distal being further from the hip joint, anterior being nearer the front of the body, posterior being nearer the back of the body, medial being nearer the centerline of the body, and lateral being further from the center line of the body. In total hip arthroplasty, the surfaces of the femur and pelvis are cut away and replaced with substitute implants. In a typical case, the implants include a hip stem component, a femoral head component, and an acetabular component.

The femoral bone is prepared by creating an opening down the intramedullary canal into the femoral bone along an axis from a proximal position at the upper end of the femur toward a distal position at the lower end of the femur. The pelvis is prepared by reaming the acetabulum. The implants may be placed directly in contact with the prepared bone surfaces for bony fixation of the implant. Alternatively, bone cement may be introduced into the prepared canal and acetabulum so that it hardens around and locks the components in place.

The hip stem component includes a stem portion extending down into the intramedullary canal of the femur and a neck portion extending away from the femur to support the femoral head component.

A recent development is the use of minimally invasive surgical techniques in which the bone is prepared and the implants inserted through small incisions that cause less trauma to surrounding muscles and other soft tissues such that the patients recovery is faster. Such minimally invasive surgical techniques can be challenging due to the difficulty in visualizing the surgical cavity and maneuvering the instruments and implants within the tight confines of the incision.

SUMMARY

The present invention provides a hip prosthesis for insertion into a femur having a proximal end adjacent a hip joint, a distal end adjacent a knee joint, an anterior side, a posterior side, a medial side, a lateral side, and an intramedullary canal.

In one aspect of the invention, the hip prosthesis includes a neck and a stem defining a longitudinal axis and having a proximal portion, a distal portion, and a transition portion extending between the proximal portion and the distal portion of the stem. The proximal portion of the stem includes an anterior locking surface, a posterior locking surface, and a lateral surface that angles toward the longitudinal axis of the stem in a proximal direction, the anterior locking surface and the posterior locking surface of the proximal portion forming a first included angle of between six degrees and twenty degrees. The transition portion of the stem has an anterior face and a posterior face that extend substantially parallel to the longitudinal axis of the stem and that form a second included angle that is less than the first included angle.

In another aspect of the invention, the hip prosthesis includes a neck and a stem defining a longitudinal axis and having a proximal portion, a distal portion, and a transition portion extending between the proximal portion and the distal portion of the stem. The proximal portion of the stem includes an anterior locking surface, a posterior locking surface, and a lateral surface, the anterior locking surface and the posterior locking surface of the proximal portion forming a first included angle of between six degrees and twenty degrees, the lateral surface of the proximal portion having an inflection point, the lateral surface angling toward the longitudinal axis of the stem in both a proximal direction from the inflection point and a distal direction from the inflection point. The transition portion of the stem has an anterior face and a posterior face that form a second included angle that is less than the first included angle.

In yet another aspect of the invention, the hip prosthesis includes a neck and a stem defining a longitudinal axis and having a proximal portion, a distal portion, and a transition portion extending between the proximal portion and the distal portion of the stem. The proximal portion of the stem includes an anterior locking surface, a posterior locking surface, and a lateral surface that angles toward the longitudinal axis of the stem in a proximal direction, the anterior locking surface and the posterior locking surface of the proximal portion forming a first included angle of between six degrees and twenty degrees, the transition portion of the stem having an anterior face and a posterior face that extend parallel to the longitudinal axis of the stem.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 1 is a perspective view of an illustrative hip stem according to the present invention;
FIG. 2 is a front elevation view of the hip stem of FIG. 1;
FIG. 3 is a section view taken along line 3-3 of FIG. 2;
FIG. 4 is a is a section view taken along line 4-4 of FIG. 2;
FIG. 5 is a is a section view taken along line 5-5 of FIG. 2;
FIG. 6 is a is a section view taken along line 6-6 of FIG. 2;
FIG. 7 is a is a section view taken along line 7-7 of FIG. 2;
FIG. 8 is a is a section view taken along line 8-8 of FIG. 2;
FIG. 9 is a is a section view taken along line 9-9 of FIG. 2;
FIG. 10 is a is a section view taken along line 10-10 of FIG. 2;
FIG. 11 is a side elevation view of the hip stem of FIG. 1; and
FIG. 12 is a section view taken along line 12-12 of FIG. 11.

DESCRIPTION OF THE ILLUSTRATIVE EXAMPLES

FIGS. 1-12 illustrate an illustrative hip stem 10 having a proximal end 12, a distal end 14, and a longitudinal axis 16 therebetween. The stem 10 includes anterior, posterior, medial, and lateral sides 18, 20, 22, 24. A neck 17 extends at an angle from the proximal end 12 of the stem 10 to support a femoral head component (not shown) in articulating with the pelvis. The present investigators have found that hip stem fixation is enhanced by designing the stem differently in each of three general portions including a proximal locking portion 40, a transition portion 80, and a distal shank 100.

The proximal locking portion 40 advantageously includes anterior and posterior locking surfaces 42, 44 that diverge from the stem axis 16 proximally as best seen in FIG. 10. The locking surfaces 42, 44 are preferably flat planar surfaces that diverge equally from the stem axis 16 to provide initial fixation. Each surface 42, 44 forms an angle with the stem axis of from 3 to 10 degrees; preferably from 5 to 10 degrees; and more preferably 7 degrees. The included angle 46 is therefore from 6-20 degrees; preferably from 10-20 degrees; and more preferably 14 degrees. At angles greater than 3 degrees, and especially within the preferred ranges, the locking surfaces 42, 44 form an anteroposterior wedge that provides rigid initial fixation and which is highly resistance to subsidence distally into the femur. The locking surfaces 42, 44 also result in axial loads on the stem 10 being advantageously transferred to the femur with a relatively larger axial component and a relatively smaller radial component than would be the case with smaller angles such that the femur is axially loaded proximally with reduced potential for femoral fracture. Finally, the locking surfaces 42, 44 result in a definitive stopping point as a surgeon is driving the stem 10 into a femur which can be felt indicating that the stem 10 is fully seated. The locking surfaces 42, 44 converge medially 47 as best seen in FIG. 9 to fit the proximal femoral geometry.

The proximal locking portion also advantageously includes a hyperbolic shaped flat relief surface 48 to better avoid stem 10 impingement with the bone during stem insertion. In particular, the relief surface 48 helps to avoid impingement with the greater trochanter. The surface 48 is created by angling the proximal portion of the lateral side 24 in toward the stem axis 16. The relief surface 48 transitions from a flat surface to a tapering cone extending distally downward toward the tip of the stem 10. Referring to FIG. 2, the relief surface 48 forms a surface that diverges from the stem axis 16 distally to an inflection point 50 which is the most lateral point on the lateral surface 24 and corresponds to the apex of the hyperbolic shaped surface 48. Thus, by moving the lateral-most point on the lateral surface 24 distally away from the proximal end 12, the present investigators have improved the insertion characteristics of the stem 10. From the inflection point 50 to the distal shank portion, the lateral surface 24 converges toward the stem axis 16 at angle α, which is a 2.5 degree angle (FIG. 12).

The proximal locking portion 40 extends from 10 to 30 percent of the overall stem length measured between the proximal and distal ends 12, 14 of the stem 10. Preferably the proximal locking portion 40 extends from 15 to 25 percent. More preferably, the locking portion 40 extends downwardly from the proximal end 12 by 20 percent of the stem length. Preferably, the proximal locking portion 40 includes a porous surface geometry 60 to promote bony ingrowth for long term fixation. In the illustrative hip stem 10, the porous surface 60 covers the proximal locking portion 40 in a continuous layer over the anterior, posterior, medial, and lateral sides 18, 20, 22, 24. The porous surface 60 extends distally into the transition portion 80 on the medial side 22 and wraps partway over the anterior and posterior sides 18, 20. Preferably, the porous surface includes a tantalum metal porous surface having a structure similar to that of natural trabecular bone. Such a material is described in U.S. Pat. No. 5,282,861 entitled "OPEN CELL TANTALUM STRUCTURES FOR CANCELLOUS BONE IMPLANTS AND CELL AND TISSUE RECEPTORS", issued to R. B. Kaplan and assigned to Ultramet. The material is fabricated of tantalum using vapor deposition. This material has been sold by Implex Corporation of Allendale, N.J., under the tradename HEDROCEL. Zimmer, Inc., with manufacturing facilities in Warsaw, Ind., sells a line of surgical implants incorporating this trabecular metal technology. The trabecular metal consists of interconnecting pores resulting in a structural biomaterial that is 80% porous and which allows much greater bone ingrowth compared to conventional porous coatings and much greater shear strength. In addition, the trabecular metal possesses a high strength-to-weight ratio. The material is produced by vapor depositing tantalum on an open celled porous matrix.

The neck 17 advantageously includes opposed flat surfaces 19 formed on it between the proximal end 12 of the stem 10 and the free end 21 of the neck 17. The flat surfaces 19 provide clearance for increased articulation of the stem relative to an acetabular component (not shown). The flat surfaces 19 further provide an engagement surface for an instrument to grip the neck 17.

The transition portion 80 of the stem 10 advantageously includes anterior and posterior faces 82, 84 to provide clearance between the stem and the cortical bone of the intramedullary canal of the femur during minimally invasive surgical procedures. In a minimally invasive hip procedure, soft tissues tend to push the stem 10 into the sides of the intramedullary canal such that the stem insertion forces are not acting straight down into the canal. These off axis forces can lead to femoral fractures. The anterior and posterior faces 82, 84 of the present invention relieve initial insertion hoop stresses making stem insertion easier and safer.

The anterior face 82 lies between the anterior locking surface 42 and the shank portion 100 and the posterior face 84 between the posterior locking surface 44 and the shank portion 100. The faces 82, 84 further lie between the medial and lateral sides 22, 24. The anterior and posterior faces 82, 84 are preferably angled relative to the stem axis at an angle shallower than the angle of the anterior and posterior locking surfaces 42, 44 and preferably at an angle shallower than the taper of the shank portion 100 which will be discussed below. Preferably the faces 82, 84 are each angled relative to the axis 16 at an angle less than 3 degrees; more preferably the faces 82, 84 are parallel to the axis 16.

The distal shank portion 100 generally forms a tapering cone having an included angle β of 3 degrees, as shown in FIG. 12. However, while maintaining the 3 degree taper angle β, the shank 100 advantageously transitions from a generally cylindrical cross section as shown in FIG. 6 to a polygonal cross section as shown in FIGS. 7 and 8. The polygonal sections include polygonal faces 102 connected by vertices 104. The faces 102 provide clearance for the shank 100 so that only the vertices 104 contact cortical bone distally to provide stem centralization while easing insertion. The vertices 104 form a press fit with the distal intramedullary canal and may be size to bite into the bone slightly to provide a degree of rotational resistance to the stem 10. The faces 102 also provide a space between the shank 100 and the intramedullary canal to relieve pressure from body fluids within the canal to minimize the possibility of an embolism upon insertion of the stem 10 into the canal.

Although examples of a hip stem prosthesis and its use have been described and illustrated in detail, it is to be understood that the same is intended by way of illustration and example only and is not to be taken by way of limitation. Accordingly, variations in and modifications to the hip stem prosthesis and its use will be apparent to those of ordinary skill in the art, and the following claims are intended to cover all such modifications and equivalents.

What is claimed is:

1. A hip prosthesis having a medial side, a lateral side, an anterior side, and a posterior side, the hip prosthesis comprising:
   a neck; and
   a stem defining a longitudinal axis and having a proximal portion, a distal portion, and a transition portion extending between the proximal portion and the distal portion of the stem, the proximal portion of the stem including an anterior locking surface, a posterior locking surface, and a lateral surface that angles toward the longitudinal axis of the stem in a proximal direction, at least a portion of the lateral surface including a porous layer, the anterior locking surface and the posterior locking surface of the proximal portion forming a first included angle of between six degrees and twenty degrees and defining a maximum width of the hip prosthesis measured between the anterior and posterior sides of the hip prosthesis, the transition portion of the stem including an anterior face and a posterior face that extend parallel to the longitudinal axis of the stem.

2. The hip prosthesis of claim 1, wherein the stem has a stem length and the proximal portion of the stem extends from 10 percent to 30 percent of the stem length.

3. The hip prosthesis of claim 1, wherein the anterior locking surface and the posterior locking surface of the proximal portion form a first included angle of between ten degrees and twenty degrees.

4. The hip prosthesis of claim 1, wherein the distal portion of the stem forms an included taper angle of approximately 3 degrees.

5. The hip prosthesis of claim 1, wherein the distal portion of the stem has a proximal cross-section defining a circle and a distal cross-section defining a polygon.

6. A hip prosthesis having a medial side, a lateral side, an anterior side, and a posterior side, the hip prosthesis comprising:
   a neck; and
   a stem defining a longitudinal axis and having a proximal portion and a distal portion and a transition portion that extends between the proximal portion and the distal portion, the proximal portion of the stem including an anterior locking surface, a posterior locking surface, and a lateral surface, at least a portion of the lateral surface including a porous layer, the anterior locking surface and the posterior locking surface of the proximal portion forming a first included angle of between ten degrees and twenty degrees and defining a maximum width of the hip prosthesis measured between the anterior and posterior sides of the hip prosthesis, the lateral surface of the proximal portion having an inflection point, the lateral surface angling toward the longitudinal axis of the stem in both a proximal direction from the inflection point and a distal direction from the inflection point, the transition portion of the stem including an anterior face and a posterior face that form a second included angle of zero degrees.

7. The hip prosthesis of claim 6, wherein the distal portion of the stem has a proximal cross-section defining a circle and a distal cross-section defining a polygon.

8. A hip prosthesis having a medial side, a lateral side, an anterior side, and a posterior side, the hip prosthesis comprising:
   a neck; and
   a stem comprising a solid substrate and a porous layer coupled to the solid substrate, the stem defining a longitudinal axis and having a proximal portion, a distal portion, and a transition portion extending between the proximal portion and the distal portion of the stem, the proximal portion of the stem including an anterior locking surface, a posterior locking surface, and a lateral surface that angles toward the longitudinal axis of the stem in a proximal direction, the lateral surface being oriented more vertically than horizontally such that, when the hip prosthesis is implanted, the lateral surface faces more in a lateral direction than in the proximal direction, the anterior locking surface and the posterior locking surface of the proximal portion forming a first included angle of between six degrees and twenty degrees, the solid substrate tapering in the proximal portion of the stem to produce the anterior and posterior locking surfaces, the anterior and posterior locking surfaces defining a maximum width of the hip prosthesis measured between the anterior and posterior sides of the hip prosthesis, the transition portion of the stem including an anterior face and a posterior face that extend substantially parallel to the longitudinal axis of the stem and that form a second included angle of zero degrees.

9. The hip prosthesis of claim 8, wherein the first included angle is fourteen degrees.

10. The hip prosthesis of claim 8, wherein the first included angle is between ten and twenty degrees.

11. The hip prosthesis of claim 8, wherein at least a portion of the proximal portion of the stem is encircled by the porous layer.

12. The hip prosthesis of claim 11, wherein the porous layer includes tantalum metal.

13. The hip prosthesis of claim 11, wherein the porous layer includes tantalum metal that has been vapor-deposited onto an open celled porous matrix.

14. The hip prosthesis of claim 8, wherein the distal portion of the stem has a proximal cross-section defining a circle and a distal cross-section defining a polygon.

15. The hip prosthesis of claim 8, wherein the distal portion of the stem forms an included taper angle of approximately 3 degrees.

16. The hip prosthesis of claim 8, wherein the lateral surface of the stem includes an inflection point, the lateral surface of the stem angling toward the longitudinal axis of the stem from the inflection point in the proximal direction.

17. A hip prosthesis having a medial side, a lateral side, an anterior side, and a posterior side, the hip prosthesis comprising:
   a neck; and
   a stem defining a longitudinal axis and having a proximal portion, a distal portion, and a transition portion extending between the proximal portion and the distal portion of the stem, the proximal portion of the stem including an anterior locking surface, a posterior locking surface, and a lateral surface, the anterior locking surface and the posterior locking surface of the proximal portion forming a first included angle of between six degrees and twenty degrees, the anterior locking surface and the posterior locking surface of the proximal portion converging medially, the stem having a continuous porous outer layer that completely surrounds the stem along the medially converging anterior and posterior locking surfaces such that a cross section of the stem through the medially converging anterior and posterior locking surfaces intersects the porous outer layer on the medial, lateral, anterior, and posterior sides of the hip prosthesis, the lateral surface of the proximal portion having an inflection point, the lateral surface angling toward the longitudinal axis of the stem in both a proximal direction from the inflection point and a distal direction from the inflection point, the transition portion of the stem including an anterior face and a posterior face that form a second included angle of zero degrees.

18. The hip prosthesis of claim 17, wherein the first included angle is fourteen degrees.

19. The hip prosthesis of claim 17, wherein the distal portion of the stem has a proximal cross-section defining a circle and a distal cross-section defining a polygon.

20. The hip prosthesis of claim 17, wherein the neck includes an anterior flat surface and a posterior flat surface, the anterior flat surface and the posterior flat surface dimensioned to mate with a corresponding insertion tool to rotationally lock the hip prosthesis to the insertion tool.

* * * * *